(12) United States Patent
Strong et al.

(10) Patent No.: US 12,364,830 B2
(45) Date of Patent: Jul. 22, 2025

(54) ENDOTRACHEAL TUBE STABILIZER

(71) Applicant: VCB IP Holdings, LLC, St. Louis, MO (US)

(72) Inventors: James Ringgold Strong, Clayton, MO (US); David Mark DeLulio, Lafayette, LA (US)

(73) Assignee: VCB Holdings, LLC

( * ) Notice: Subject to any disclaimer, the term of this patent is extended or adjusted under 35 U.S.C. 154(b) by 715 days.

(21) Appl. No.: 17/277,785

(22) PCT Filed: Sep. 19, 2019

(86) PCT No.: PCT/US2019/051931
§ 371 (c)(1),
(2) Date: Mar. 19, 2021

(87) PCT Pub. No.: WO2020/061311
PCT Pub. Date: Mar. 26, 2020

(65) Prior Publication Data
US 2021/0346628 A1 Nov. 11, 2021

Related U.S. Application Data

(60) Provisional application No. 62/733,182, filed on Sep. 19, 2018.

(51) Int. Cl.
*A61M 16/04* (2006.01)

(52) U.S. Cl.
CPC .............................. *A61M 16/0497* (2013.01)

(58) Field of Classification Search
CPC ............................ A61M 16/0497; F16L 3/10
See application file for complete search history.

(56) References Cited

U.S. PATENT DOCUMENTS

| | | | | |
|---|---|---|---|---|
| 3,602,227 A * | 8/1971 | Andrew | ................ | A61M 25/02 248/49 |
| 3,760,811 A | 9/1973 | Andrew | | |
| 4,744,358 A * | 5/1988 | McGinnis | ......... | A61M 16/0497 128/DIG. 26 |
| 5,398,679 A * | 3/1995 | Freed | .................... | A61M 25/02 128/912 |
| 7,000,609 B2 * | 2/2006 | Kleen | ..................... | F16L 3/237 24/527 |
| 8,636,008 B2 * | 1/2014 | Flory | ................ | A61M 16/0493 128/207.14 |

(Continued)

FOREIGN PATENT DOCUMENTS

| | | |
|---|---|---|
| CN | 205434624 U | 8/2016 |
| CN | 106422028 A | 2/2017 |

(Continued)

*Primary Examiner* — Timothy A Stanis
*Assistant Examiner* — Kira B Daher

(57) ABSTRACT

An endotracheal tube stabilizer comprising a stabilization bar; and a tube cradle comprising a first component having a concave portion, the first component coupled to the stabilization bar; a second component having a concave portion; and a securing element adapted to selectively maintain the first component at a fixed location relative to the second component, wherein the first and second components are adapted to translate toward one another in a linear direction transverse to the concave portions.

19 Claims, 4 Drawing Sheets

(56) References Cited

U.S. PATENT DOCUMENTS

| | | | |
|---|---|---|---|
| 11,612,710 B2 * | 3/2023 | Jockel | A61M 16/0493 128/207.17 |
| 2002/0026936 A1 * | 3/2002 | Kirn | A61M 25/013 128/200.24 |
| 2008/0202529 A1 | 8/2008 | Flory et al. | |
| 2011/0220127 A1 * | 9/2011 | Chang | A61M 16/0488 128/207.14 |
| 2011/0284008 A1 * | 11/2011 | Kanowitz | A61M 16/0488 128/207.17 |
| 2013/0068233 A1 * | 3/2013 | De Lulio | A61M 16/0497 128/207.17 |
| 2018/0099112 A1 * | 4/2018 | Belenkiy | A61M 16/0497 |

FOREIGN PATENT DOCUMENTS

| | | |
|---|---|---|
| EP | 2014327 A1 | 1/2009 |
| WO | 2016116916 A1 | 7/2016 |

* cited by examiner

ENDOTRACHEAL TUBE STABILIZER

This application is a U.S. National Phase Application of International Application No. PCT/US2019/051931 filed on Sep. 19, 2019, which claims the benefit of priority from U.S. Provisional Patent Application No. 62/733,182 filed on Sep. 19, 2018. The disclosures of which are incorporated herein by reference.

FIELD OF THE DISCLOSURE

The present disclosure relates to endotracheal tube stabilizers.

RELATED ART

Adjustment of endotracheal tubes within traditional endotracheal tube stabilizers generally requires significant user operation and input, taking time and reducing effectiveness of medical practitioners in safely caring for patients, such as neonates.

Securing the endotracheal tube to the endotracheal tube stabilizer is typically done by an adhesive backed tape wrapped and adhered to both the endotracheal tube and the endotracheal tube stabilizer. To adjust the position of the endotracheal tube requires significant time detaching and reattaching the endotracheal tube to the endotracheal tube stabilizer. Moreover, the use of adhesive backed tapes can deform the endotracheal tube, altering fluid flow characteristics.

The medical industry continues to demand improved endotracheal tube stabilizers capable of rapidly realigning endotracheal tubes while simultaneously maintaining integrity of the endotracheal tube and preventing deformation thereof.

BRIEF DESCRIPTION OF THE DRAWINGS

Embodiments are illustrated by way of example and are not intended to be limited in the accompanying figures.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. As used herein, a "fluid" refers to any liquid or gaseous material. The materials, methods, and examples are illustrative only and not intended to be limiting. To the extent not described herein, many details regarding specific materials and processing acts are conventional and may be found in textbooks and other sources within the endotracheal tube stabilizer and medical arts.

Endotracheal tube stabilizers in accordance with one or more of the embodiments described herein can generally include a stabilization bar and a tube cradle. The tube cradle can be coupled to the stabilization bar. The tube cradle can include two components each having a concave portion combined to form an aperture. An endotracheal tube may be positioned within the aperture and secured therein to prevent longitudinal translation of the endotracheal tube relative to the endotracheal tube stabilizer.

Figure 1:
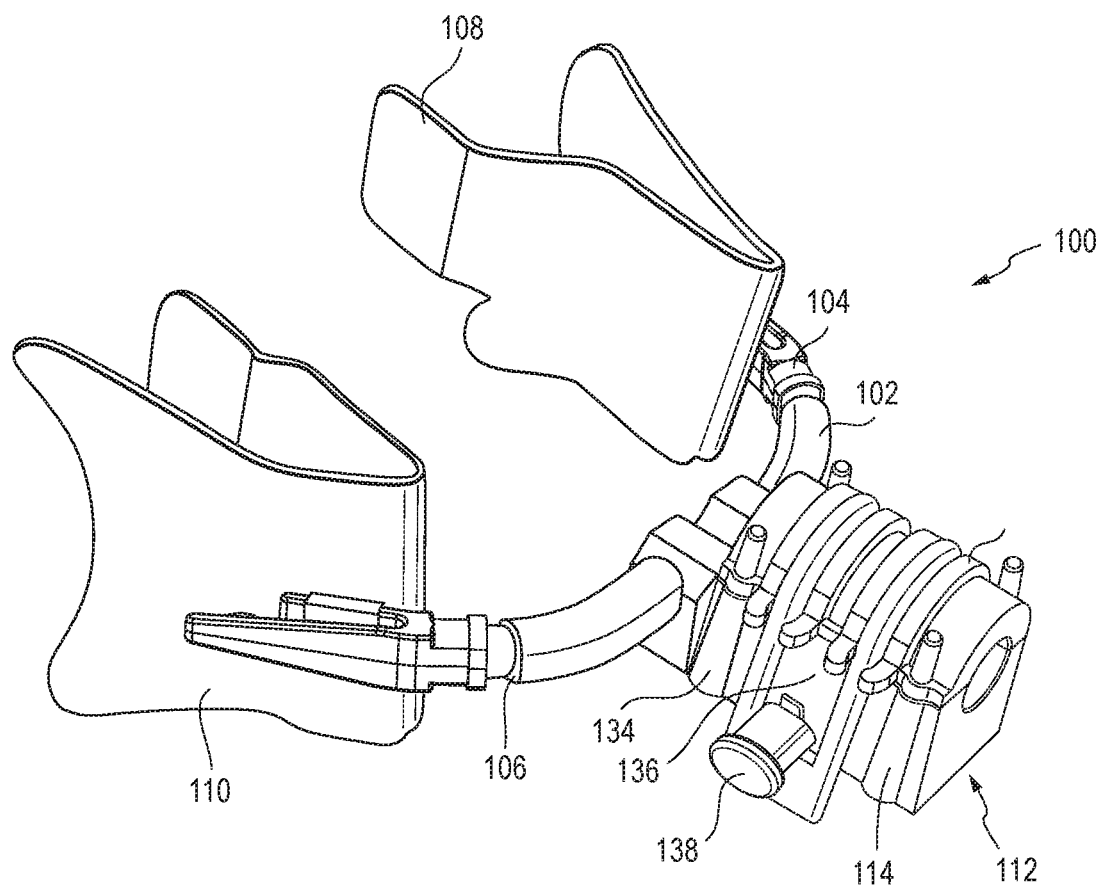
FIG. 1 includes a perspective view of an endotracheal tube stabilizer in accordance with an embodiment.
Figure 2:
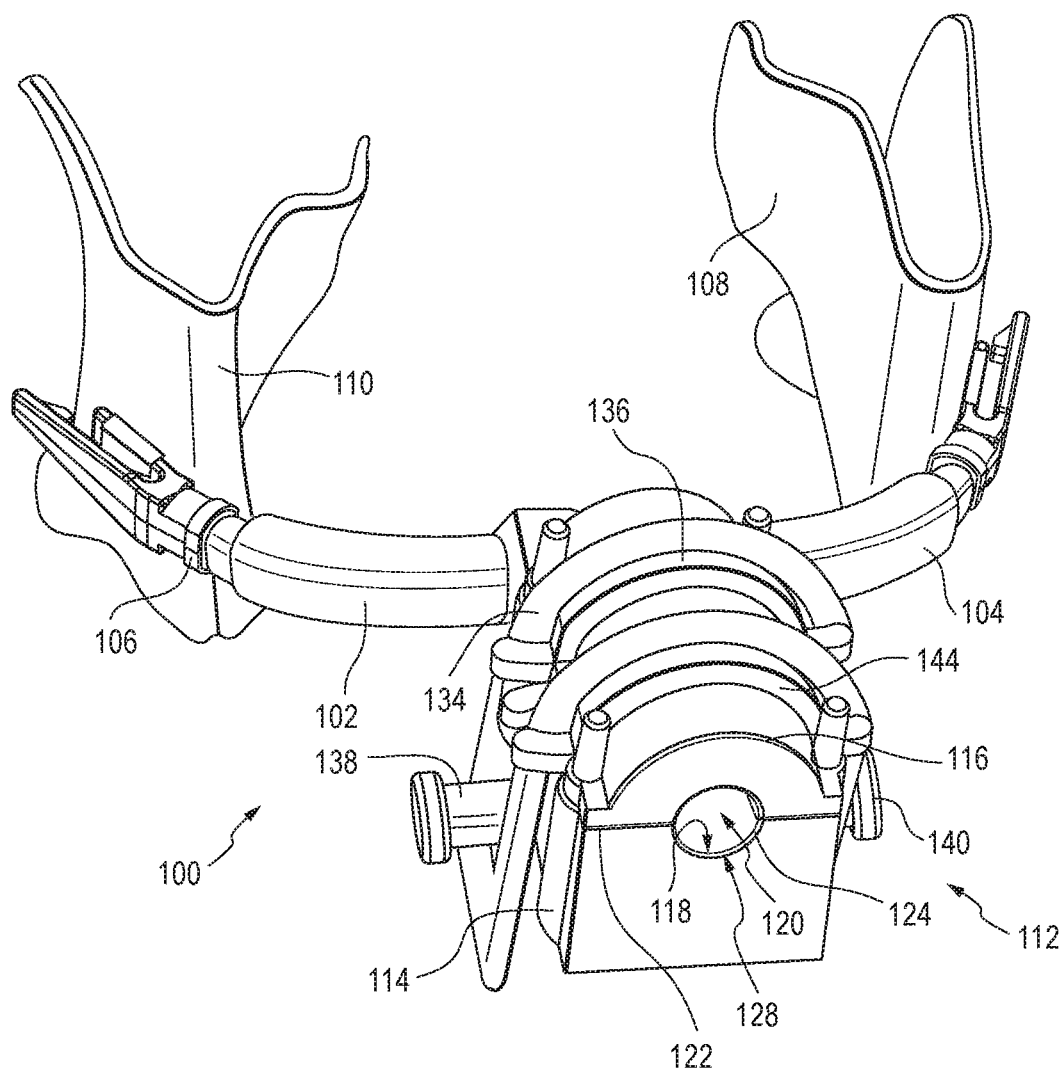
FIG. 2 includes a perspective view of the endotracheal tube stabilizer in accordance with an embodiment.

Referring initially to FIGS. 1 and 2, an endotracheal tube stabilizer 100 can generally include a stabilizer bar 102 having a length, as measured between opposing axial ends 104 and 106. A first cheek pad 108 can operatively couple with the stabilizer bar 102 at the first axial end 104 and a second cheek pad 110 can operatively couple with the stabilizer bar 102 at the second axial end 106. The first and second cheek pads 108 and 110 can be removably engaged with skin of a patient, e.g., by an adhesive, such that the stabilizer bar 102 can be selectively held at a fixed relative location with respect to a patient requiring oral intubation.

In an embodiment, the cheek pads 108 and 110 are adapted to be removably coupled with the stabilizer bar 102. In a more particular embodiment, the stabilizer bar 102 can be disconnected from one or both of the cheek pads 108 and 110. Removable coupling may be facilitated by one or more detachable elements or fasteners, such as for example a ratcheting system, a threaded or nonthreaded fastener, a bayonet connection, an interference fit, a snap fit, any other suitable coupling element, or any combination thereof. In another embodiment, at least one of the cheek pads 108 or 110 is fixedly coupled with the stabilization bar 102.

In a particular embodiment, the stabilizer bar 102 can include a flexible material. Exemplary materials include metals, polymers, and combinations thereof. In a more particular embodiment, the stabilizer bar 102 can include a metal wire at least partially encapsulated by a non-metal material, such as a polymeric material (e.g., an elastomer). In an embodiment, the metal wire can include a non-magnetic metal. Shaping of the stabilizer bar 102 to fit the patient can occur in situ or prior to attachment of the endotracheal tube stabilizer 100 to the patient. In an embodiment, the stabilizer bar 102 can be adapted to plastically deform so as to remain in the selected configuration when engaged with the patient.

In an embodiment, a tube cradle 112 is coupled to the stabilizer bar 102. The tube cradle 112 can receive and secure an endotracheal tube. In a particular embodiment, the tube cradle 112 is disposed at a central location along the stabilizer bar 102. In a more particular embodiment, the tube cradle 112 is disposed equidistant between the axial ends 104 and 106 of the stabilizer bar 102. In another embodiment, the tube cradle 112 can be offset from a central location of the stabilizer bar.

In an embodiment, the tube cradle 112 can have an oblong shape. In another embodiment, the tube cradle 112 can have a tear drop shape. In yet another embodiment, the tube cradle 112 has a cuboidal body. In a particular embodiment, the tube cradle 112 can have square edges. In another particular embodiment, the tube cradle 112 can have rounded edges, chamfered edges, or any combination thereof. In yet further embodiments, the tube cradle can have curved surfaces, planar surfaces, or combinations thereof. In an embodiment, the tube cradle 112 can be overmolded to the stabilizer bar 102. In another embodiment, the tube cradle 112 can be attached to the stabilizer bar 102 by use of an adhesive, mechanical fastener, another suitable fastening technique, or any combination thereof In an embodiment, the tube cradle 112 includes a first component 114 and a second component 116. In certain instances, the first and second components 114 and 116 can be detached from one another. More particularly, the first and second portions 114 and 116 can be freely moved with respect to one another. In other instances, the first and second components 114 and 116 can be coupled together. For example, in an embodiment, the first and second components 114 and 116 can be coupled together by a hinge, a deformable member, or another intermediate element. In a particular embodiment, the first and second components 114 and 116 can rotate (e.g., pivot) with respect to one another about a rotational axis parallel with an aperture (described below) of the tube cradle 112. In another embodiment, the rotational axis can be perpendicular with the aperture, or otherwise angularly offset therefrom.

At least one of the first and second components 114 or 116 can include a generally cuboidal shape. In a particular embodiment, the first and second components 114 and 116 can have similar shapes as compared to one another. In an embodiment, the first and second components 114 and 116 are detachable from one another. In such a manner, the first and second components 114 and 116 can be separated from one another. In an embodiment, the first component 114 can be fixedly coupled to the stabilizer bar 102 and the second component 116 can be detachable from the first component 114.

The first and second components 114 and 116 can each include a concave portion 118 and 120, respectively (FIG. 2). The concave portions 118 and 120 can have the same, or similar, shapes, sizes, or other attributes as compared to one another. In an embodiment, at least one of the concave portions 118 and 120 can have at least one right-angled edge. In another embodiment, at least one of the concave portions 118 and 120 can have rounded edges, chamfered edges, or any combination thereof. In a particular embodiment, the concave portions 118 and 120, together, define an aperture 124 adapted to receive an endotracheal tube. In certain instances, use of non-right angled edges along at least one of the concave portions 118 and 120 can facilitate easier alignment with the endotracheal tube.

The concave portions 118 and 120 can be recessed into the first and second components 114 and 116, respectively. In an embodiment, the concave portions 118 and 120 are recessed from flat, or generally flat, surfaces 122 of the first and second components 114 and 116. In another embodiment, the concave portions 118 and 120 can include edges that are adapted to contact one another when the first and second components 114 and 116 are closed to form a continuous aperture 124. In an embodiment, an edge of at least one of the concave portions 118 and 120 can be rounded or beveled. In another embodiment, the edge of at least one of the concave portions 118 and 120 can include an approximately 90° edge with respect to the flat, or generally flat, surface 122 of the first or second component 114 or 116.

In an embodiment, the concave portions 118 and 120 extend along the surfaces 122 of the first and second components 114 and 116 in a direction generally normal to the stabilizer bar 102 at the interface of the stabilizer bar 102 and tube cradle 112. In an embodiment, the concave portions 118 and 120 extend across the entire length of the tube cradle 112.

In an embodiment, the concave portions 118 and 120 are generally similar in size and relative shape as compared to one another. The concave portions 118 and 120 can define generally hemicylindrical volumes which, when combined, create the aperture 124 adapted to receive and secure an endotracheal tube to the endotracheal tube stabilizer 100. In an embodiment, the aperture 124 can be cylindrical, or generally cylindrical, so as to accommodate a cylindrical endotracheal tube. In another embodiment, the aperture 124 can have an otherwise ellipsoidal shape, e.g., an oval. In yet a further embodiment, the aperture 124 can be at least partially polygonal. That is, the aperture 124 can have at least one planar segment, as viewed along the length of the aperture 124.

In an embodiment, the aperture 124, or a best fit circle thereof, can have a diameter, $D_A$, equal to or less than an outer diameter, $D_{ET}$, of an endotracheal tube. For example, in an embodiment $D_A$ is no greater than 1.0 $D_{ET}$, such as no greater than 0.99 $D_{ET}$, or no greater than 0.98 $D_{ET}$, or no greater than 0.97 $D_{ET}$, or no greater than 0.96 $D_{ET}$, or no greater than 0.95 $D_{ET}$, or no greater than 0.9 $D_{ET}$, or no greater than 0.85 $D_{ET}$, or no greater than 0.8 $D_{ET}$.

In another embodiment, the aperture 124, or a best fit circle thereof, can have a larger diameter than the outer diameter, $D_{ET}$, of the endotracheal tube.

In an embodiment, the cross-sectional shape of the aperture 124 varies along the length of the aperture 124. For example, the aperture 124 can have a cylindrical, or generally cylindrical, cross-sectional shape at a first longitudinal position, and a polygonal shape at a second longitudinal position. In another embodiment, the cross-sectional shape is constant, or generally constant, along the length of the aperture 124.

In an embodiment, a central axis of the aperture 124 lies along a straight, or generally straight, line. In another embodiment, the central axis of the aperture 124 lies along an arcuate line.

Figure 3:
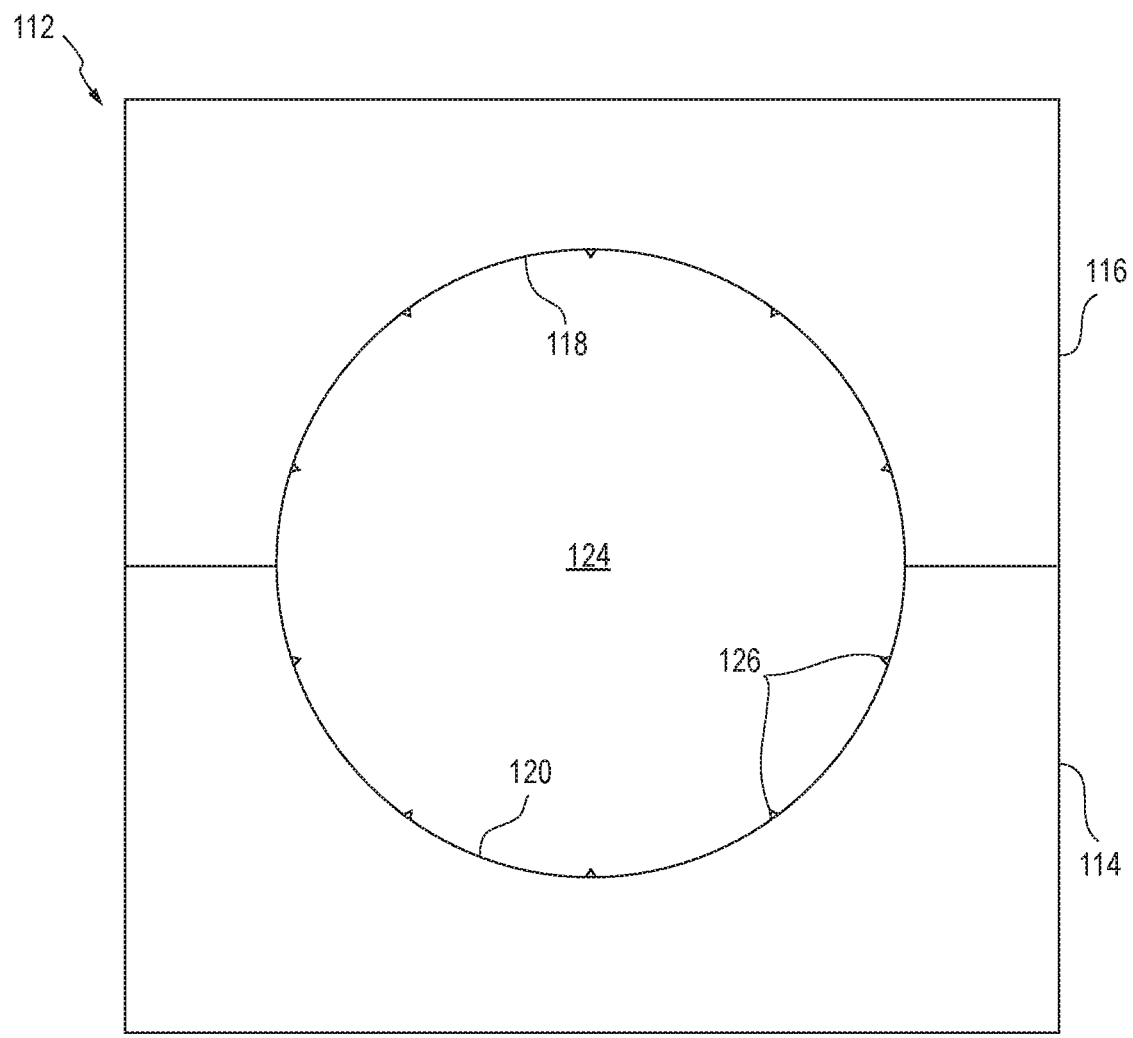
FIG. 3 includes a side elevation view of a tube cradle of the endotracheal tube stabilizer in accordance with an embodiment FIG. 4 includes a perspective view of the endotracheal tube stabilizer in accordance with another embodiment.

Referring to FIG. 3, in a particular embodiment, at least one, such as both, of the concave portions 118 and 120 include one or more elements 126 extending toward the central axis of the aperture 124. The elements 126 can enhance grip with the endotracheal tube. In a particular instance, the elements 126 can deform the outside diameter or surface of the endotracheal tube. The elements 126 can increase frictional resistance between the endotracheal tube and the aperture 124.

In an embodiment, the elements 126 are circumferentially spaced apart around the surface of the aperture 124. In a particular embodiment, a set of elements 126 can extend along a line extending around the circumference of the endotracheal tube in a direction perpendicular to the length of the endotracheal tube. In another particular embodiment, a set of elements 126 can extend around the aperture 124 in a helical, undulating, arcuate, castellated, wavy, or otherwise non-perpendicular, circumferential pattern. The elements 126 can have rounded or otherwise arcuately contoured tips to prevent piercing of the endotracheal tube.

In an embodiment, the elements 126 can define a best fit circle having a diameter less than the diameter of the endotracheal tube in the undeformed state (with no radially inward force therealong).

In an embodiment, the elements 126 can be replaced by a generally textured portion, e.g., a surface of the aperture 124 having a suitable surface roughness. In a particular embodiment, the generally textured portion can include ribs, projections, roughened surfaces, castellations, undulations, serrations, bumped, and other suitable textured portions may enhance grip of the tube cradle 112 with the endotracheal tube. Secure engagement of the endotracheal tube may prevent the endotracheal tube from undesirably moving, thus avoiding infliction of physical trauma to vital organs of the patient and malposition of the endotracheal tube.

Referring again to FIG. 2, in an embodiment, the aperture 124 has a tapered (flared) portion 128. The tapered portion 128 can be disposed at an axial end of the aperture 124.

The tapered portion 128 can have the same dimension as the aperture 124 at a first end of the tapered portion 128 and become wider toward the longitudinal end of the aperture 124. In such a manner, the endotracheal tube can bend at the longitudinal end of the aperture 124. This may reduce occurrence of pinching of the endotracheal tube upon application of force to the endotracheal tube transverse to the central axis of the aperture 124. Such pinching may reduce fluid flow through the endotracheal tube, cutting off circulation of fluids to the patient.

In an embodiment, the endotracheal tube stabilizer 100 is adapted to contact an endotracheal tube along at least 75% of the circumference of the endotracheal tube. That is, the endotracheal tube stabilizer 100 can contact the endotracheal tube along at least 75% of a circumferential line extending around the endotracheal tube. In another embodiment, the endotracheal tube stabilizer 100 is adapted to contact at least 80% of the circumference of the endotracheal tube, or at least 90% of the circumference of the endotracheal tube, or at least 99% of the endotracheal tube. In a particular embodiment, the endotracheal tube stabilizer 100 is adapted to contact the endotracheal tube along the entire circumference of the endotracheal tube.

In an embodiment, the aperture 124 has a length, $L_A$, and the surface of the aperture 124 is adapted to have 360 degree contact with the endotracheal tube along at least 0.2 $L_A$, or at least 0.5 $L_A$, or at least 0.8 $L_A$, or at least 0.9 $L_A$, or at least 0.99 $L_A$.

Figure 4:
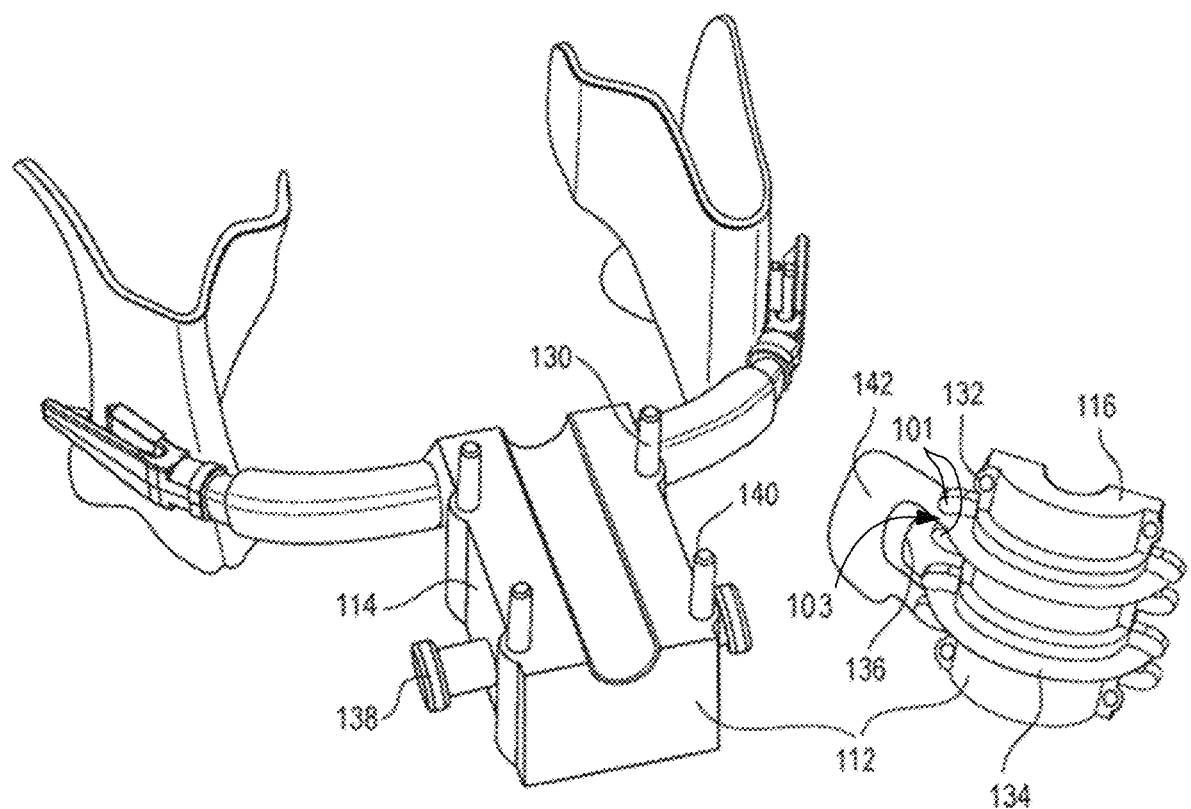

Referring to FIG. 4, in an embodiment the tube cradle 112 further includes at least one post 130 and at least one recess 132 adapted to receive the at least one post 130. In a particular embodiment the post 130 can extend from the first or second components 114 or 116 and the recess 132 can extend into the other of the first or second component 114 or 116. In an embodiment, the at least one post 130 has a length extending perpendicular to the surface of the first or second component 114 or 116. The at least one post 130 can include at least two posts, or at least three posts, or at least four posts, or at least five posts, or at least ten posts.

Each post 130 can be receivable in a complementary recess 132 formed in the other of the first and second components 114 and 116. In such a manner, the first and second components 114 and 116 can be aligned prior to fully engaging the endotracheal tube, i.e., prior to securing the endotracheal tube within the aperture 124. The scope of the disclosure is not intended to be limited by the number or orientation of the posts and recesses. For example, the posts and recesses 130 and 132 may be angularly offset from the surface of the first and second components 114 and 116.

After the posts 130 are partially installed within the complementary recesses 132, the first and second components 114 and 116 can be translated toward one another in a linear direction. This ensures proper alignment between the first and second components 114 and 116, reducing pinching of the endotracheal tube which may occur if the first and second components 114 and 116 are not properly aligned or if the first and second components 114 and 116 are engaged pivotally around a hinge or another non-linear axis. In an embodiment, the posts 130 and recesses 132 can be disposed immediately adjacent to the concave portions of the first and second components 114 and 116.

In an embodiment, at least one of the recesses 132 can have a larger diameter than the corresponding post 130 to be received therein. For example, at least one of the posts 130 can have a diameter, $D_P$, and the corresponding recess 132 can have a bore diameter, $D_R$, where $D_P$ is less than 1.0 $D_R$, such as less than 0.99 $D_R$, less than 0.95 $D_R$, less than 0.90 $D_R$, or even less than 0.8 $D_R$. In an embodiment, $D_P$ is no less than 0.1 $D_R$, such as no less than 0.25 $D_R$. Use of an oversized recess 132 may facilitate easier initial alignment between the first and second components 114 and 116.

At least one of the recesses 132 can include a tapered guide portion (not illustrated) to facilitate alignment between the recesses 132 and posts 130. The guide portion can include a funnel or generally frustoconical shape for receiving and aligning the posts 130 with the recesses 132. In another embodiment, the posts 130 can include a tapered end portion to facilitate alignment with the recesses 132. In a particular embodiment, the guide portion can extend along at least 25% of the length of the post or recess, such as at least 30% of the length, at least 35% of the length, at least 40% of the length, at least 50% of the length, at least 60% of the length, at least 70% of the length, at least 80% of the length, or even at least 90% of the length. In a particular embodiment, the tapered or guide portion may extend along the entire length of the post 130 or recess 132.

Once assembled, at least one of the posts 130 can extend an entire distance through the corresponding recess(es) 132. In an embodiment, at least one of the posts 130 can extend a distance beyond the recess(es) 132 such that a portion of the post 130 is visible beyond the recess(es) 132. In another embodiment, at least one of the posts 130 can have a length that is less than the length of the corresponding recess(es) 132. That is, the posts 130 can be shorter than the length of the recesses 132. In an embodiment, the posts 130 all have uniform shapes or sizes. In another embodiment, at least one of the posts 130 can have a different size or shape as compared to another one of the posts 130.

In an embodiment, posts 130 and recesses 132 are disposed on both sides of the aperture 124. For example, at least one post can be disposed on a first side of the aperture 124 and at least one post can be disposed on a second, opposite, side of the aperture 124. In an embodiment, at least three posts 130 lie along a straight line. In another embodiment, the posts 130 and recesses 132 can be staggered with respect to one another such that at least three posts do not lie along a same straight line. In a further embodiment, at least two sets of posts 130 are equally spaced apart from one another. In yet another embodiment, at least two sets of posts 130 are spaced apart from one another by different distances.

In an embodiment, at least one of the posts 130 comprises a discrete element engaged with the first or second component 114 or 116. In another embodiment, at least one of the posts 130 is monolithic with the first or second component 114 or 116.

An engagement element 134 can secure the first and second components 114 and 116 together. By way of a non-limiting example, the engagement element 134 can include a ring having an internal opening 136. The opening 136 can engage with a tab 138 extending from at least one of the first and second components 114 and 116. In an embodiment, the ring can extend around at least a portion of the first or second components 114 or 116 and engage with the same tab 138 or a different tab 140. In another embodiment, the engagement element 134 can include a strip of material having an engagement feature such as a hook or loop adjacent to an end thereof to secure the engagement element to the first and second components 114 and 116. In yet a further embodiment, the engagement element 134 can include a clip, fastener, bayonet connection, interference fit, snap connector, buckle, clasp, or any other suitable fastener. In an embodiment, the compressive securing force between the first and second components 114 and 116 is not transferred to the endotracheal tube in a manner that deforms the endotracheal tube because of the material stiffness of the first and second components 114 and 116.

In an embodiment, the engagement element 134 is coupled with one or both of the first and second components 114 and 116 prior to securing an endotracheal tube. In a more particular embodiment, the engagement element 134 can be connected or integral with one or both of the first and second components 114 and 116.

In an embodiment, the engagement element 134 can first be secured to the tab 138. The engagement element 134 can be extended around the circumference of the tube cradle 112 and engaged with the same tab 138 or a different tab 140 located at a different position along the tube cradle 112. The engagement element 134 can include one or more gripping elements 142 to permit user grasp thereof. The gripping element 142 can be ribbed, contoured, textured, or otherwise shaped to facilitate easy grip thereof.

Endotracheal tube stabilizers 100 in accordance with embodiments described herein can be used to secure an endotracheal tube at a relatively fixed position with respect to a patient. The cheek pads 108 and 110 can first be attached to the skin of the patient. The stabilizer bar 102 can be shaped to correspond to the patient's face. With the first and second components 114 and 116 spaced apart from one another, the endotracheal tube can be positioned within the concave portion 118. In an embodiment, the endotracheal tube is spaced apart from at least one of the posts 130 of the first or second component 114 or 116 when positioned in the concave portion 118. In another embodiment, the endotracheal tube contacts at least one of the posts 130 of the first or second component 114 or 116 when positioned in the concave portion 118. After positioning the endotracheal tube within the concave portion 118, the second component 116 is introduced to the first component 114. The posts 130 are aligned with corresponding recesses 132 and force can be applied to one or both of the first and second components 114 and 116 to linearly translate the first and second components 114 and 116 together. As the posts 130 translate within the recesses 132, the inner surfaces of the concave portions 118 and 120 contact the endotracheal tube. Further pressure is applied until the first and second components 114 and 116 seat, or nearly seat, together. The engagement element 134 can then be coupled to the tube cradle 112, securing the first and second components 114 and 116 together. Guide portions 144 can guide the engagement element 134 to proper alignment relative to the tube cradle 112. The guide portion includes at least one pair of fingers 101 canted towards one another to define a slot 103. The slot 103 is an area through which the engagement element 134 extends when engaged with the first and second tabs 138, 140. The above-described method is intended as an exemplary process flow of use. Other steps can be included and the order of operations is not intended to be limited to the above.

In certain embodiments, the endotracheal tube stabilizer 100 can include an outer layer, such as, for example, an elastomeric coating or another suitable polymeric coating. Exemplary polymers for the outer layer include, for example, low friction polymers (e.g., fluoropolymers or PEAK) and elastomers. The outer layer may prevent deterioration of the stabilizer bar 102, the tube cradle 112, or any other component of the endotracheal tube stabilizer 100, for example, as caused by corrosion, exposure to medical waste, or any other chemical or biological material(s).

In a non-illustrated embodiment, the tube stabilizer 100 can include a selectively operable portion adapted to permit rotation, translation, or a combination thereof of a portion of the tube stabilizer 100 with respect to another portion of the tube stabilizer 100. For example, by way of a non-limiting example, the stabilizer bar 102 can be coupled with the tube cradle 112 by way of a pivot point adapted to operate as a hinge. In such a manner, the tube cradle 112 can be opened from the stabilizer bar 102, for example, during emergencies. In another embodiment, the stabilizer bar 102, tube cradle 112, cheek pad 108 or 110, or any combination thereof can include a selectively operable portion adapted to permit release or movement therebetween or within. In such a manner, a medical practitioner can readily operate on the tube stabilizer 100 in a desired manner.

Endotracheal tube stabilizers in accordance with one or more of the embodiments described herein can be operatively attached, e.g., to the skin of a patient, by attaching a stabilizer bar to cheek pads. The cheek pads can then be positioned at suitable locations relative to the patient. The stabilizer bar can be bent prior to engagement with the cheek pads. Alternatively, the stabilizer bar can be bent after engagement with the cheek pads. Bending of the stabilizer bar can allow a medical practitioner to properly shape the stabilizer bar to a suitable configuration taking into account the size and position of the cheek pads. The endotracheal tube stabilizer can then be attached to the skin of the patient.

The endotracheal tube can be inserted into the patient and partially installed within the concave portion of one or both of the first and second components. Upon proper alignment, the first and second components can be brought together in a manner as discussed above to secure the endotracheal tube relative to the patient. The engagement element can then secure the first and second components together, fixedly securing the endotracheal tube at a relatively static position with respect to the patient.

In practice, the patient may be imaged, e.g., by magnetic resonance imaging or x-ray, to determine whether the endotracheal tube is properly positioned. In cases where the endotracheal tube is not properly positioned, the engagement element can be partially, or wholly, removed and the endotracheal tube may be slid within the aperture to a suitable position. In particular embodiments, it may be further necessary to translate the first and second components at least slightly apart to permit longitudinal translation of the endotracheal tube. In other embodiments, detachment of the engagement element without further manipulation may be satisfactory to permit longitudinal translation. The posts and recesses can maintain the first and second components at a relatively fixed location with respect to one another.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the embodiments as listed below.

Embodiment 1. An endotracheal tube stabilizer comprising:
 a stabilization bar; and
 a tube cradle comprising:
 a first component having a concave portion, the first component coupled to the stabilization bar;
 a second component having a concave portion; and
 a securing element adapted to selectively maintain the first component at a fixed location relative to the second component,
 wherein the first and second components are adapted to translate toward one another in a linear direction transverse to the concave portions.

Embodiment 2. An endotracheal tube stabilizer comprising:
 a stabilization bar;
 a tube cradle comprising:
 a first component, the first component coupled to the stabilization bar; and
 a second component,
 wherein the first and second components together define an aperture adapted to receive an endotracheal tube, and wherein the aperture is closable upon translating the first and second components toward one another in a linear direction transverse to the aperture.

Embodiment 3. An endotracheal tube stabilizer comprising:
 a stabilization bar; and
 a tube cradle comprising:
 a first component having a concave portion, the first component coupled to the stabilization bar; and
 a second component having a concave portion,
 wherein the first and second components are disconnected from one another, and wherein the concave portions together define an aperture adapted to receive an endotracheal tube.

Embodiment 4. The endotracheal tube stabilizer according to any one of the preceding embodiments, wherein the tube cradle is disposed at a central location along the stabilization bar.

Embodiment 5. The endotracheal tube stabilizer according to any one of the preceding embodiments, wherein the first component comprises a concave portion, wherein the second component comprises a concave portion, and wherein the concave portions of the first and second components together define an aperture adapted to receive an endotracheal tube.

Embodiment 6. The endotracheal tube stabilizer according to embodiment 5, wherein the concave portions of the first and second components have a same volumetric capacity.

Embodiment 7. The endotracheal tube stabilizer according to any one of embodiments 5 and 6, wherein the concave portion of the first component is hemicylindrical.

Embodiment 8. The endotracheal tube stabilizer according to any one of embodiments 5-7, wherein the concave portion of the second component is hemicylindrical.

Embodiment 9. The endotracheal tube stabilizer according to any one of embodiments 5-8, wherein the aperture defines an average diameter less than a diameter of the endotracheal tube.

Embodiment 10. The endotracheal tube stabilizer according to embodiment 9, wherein the aperture diameter is no greater than 0.99 the diameter of the endotracheal tube, such as no greater than 0.98 the diameter of the endotracheal tube, no greater than 0.97 the diameter of the endotracheal tube, no greater than 0.96 the diameter of the endotracheal tube, no greater than 0.95 the diameter of the endotracheal tube, no greater than 0.94 the diameter of the endotracheal tube, no greater than 0.93 the diameter of the endotracheal tube, no greater than 0.92 the diameter of the endotracheal tube, no greater than 0.91 the diameter of the endotracheal tube, no greater than 0.90 the diameter of the endotracheal tube, no greater than 0.8 the diameter of the endotracheal tube, or even no greater than 0.7 the diameter of the endotracheal tube.

Embodiment 11. The endotracheal tube stabilizer according to any one of embodiments 5-10, wherein the aperture is cylindrical.

Embodiment 12. The endotracheal tube stabilizer according to any one of the preceding embodiments, wherein the endotracheal tube stabilizer further comprises:
 at least one post extending from one of the first and second components; and
 at least one recess extending into the other of the first and second components,
 wherein the at least one post is receivable in the at least one recess.

Embodiment 13. The endotracheal tube stabilizer according to embodiment 12, wherein the at least one post comprises at least 2 posts, such as at least 3 posts, at least 4 posts, at least 5 posts, at least 6 posts, at least 10 posts, or any other number of posts.

Embodiment 14. The endotracheal tube stabilizer according to any one of embodiments 12 and 13, wherein the at least one recess comprises at least 2 recesses, such as at least 3 recesses, at least 4 recesses, at least 5 recesses, at least 6 recesses, or even at least 10 recesses.

Embodiment 15. The endotracheal tube stabilizer according to any one of embodiments 12-14, wherein the at least one recess extends entirely through the first or second component.

Embodiment 16. The endotracheal tube stabilizer according to any one of embodiments 12-15, wherein the at least one post extends from the first or second component in a direction normal to a surface from which the posts extends from.

Embodiment 17. The endotracheal tube stabilizer according to any one of embodiments 12-16, wherein at least one of the at least one posts is disposed on a first side of the concave surface, and wherein at least one of the at least one posts is disposed on a second side of the concave surface.

Embodiment 18. The endotracheal tube stabilizer according to any one of embodiments 12-17, wherein the first component has a thickness, wherein the second component has a thickness, and wherein a length of the at least one post is different from the thicknesses of the first and second components.

Embodiment 19. The endotracheal tube stabilizer according to embodiment 18, wherein the length of the at least least one post is less than the thicknesses of the first and second components.

Embodiment 20. The endotracheal tube stabilizer according to any one of embodiments 12-17, wherein the first component has a thickness, wherein the second component has a thickness, and wherein a length of the at least one post is the same as a thickness of at least one of the first and second components.

Embodiment 21. The endotracheal tube stabilizer according to any one of embodiments 12-20, wherein the at least one post and the at least one recess are adapted to align the first and second components with one another.

Embodiment 22. The endotracheal tube stabilizer according to any one of the preceding embodiments, wherein the first component is disconnected from the second component.

Embodiment 23. The endotracheal tube stabilizer according to any one of embodiments 12-22, wherein the at least one post and the at least one recess extend in a direction generally perpendicular to a length of the aperture.

Embodiment 24. The endotracheal tube stabilizer according to any one of the preceding embodiments, wherein the endotracheal tube stabilizer further comprises:

an engagement element adapted to secure the first and second components together.

Embodiment 25. The endotracheal tube stabilizer according to embodiment 24, wherein the engagement element comprises a material different than a material of the first or second components.

Embodiment 26. The endotracheal tube stabilizer according to any one of embodiments 24 and 25, wherein the engagement element comprises an elastomer.

Embodiment 27. The endotracheal tube stabilizer according to any one of embodiments 24-26, wherein the engagement element is adapted to secure with at least one of the first and second components.

Embodiment 28. The endotracheal tube stabilizer according to any one of embodiments 24-27, wherein the engagement element comprises an O-ring.

Embodiment 29. The endotracheal tube stabilizer according to any one of embodiments 24-28, wherein the engagement element is adapted to secure with a tab projecting from at least one of the first and second components.

Embodiment 30. The endotracheal tube stabilizer according to any one of embodiments 24-29, wherein the engagement element further comprises an extension, and wherein the extension permits a user to grasp the engagement element and secure the engagement element with the first or second components.

Note that not all of the features described above are required, that a portion of a specific feature may not be required, and that one or more features may be provided in addition to those described. Still further, the order in which features are described is not necessarily the order in which the features are installed.

Certain features are, for clarity, described herein in the context of separate embodiments, may also be provided in combination in a single embodiment. Conversely, various features that are, for brevity, described in the context of a single embodiment, may also be provided separately or in any subcombinations.

Benefits, other advantages, and solutions to problems have been described above with regard to specific embodiments, However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or any change may be made without departing from the scope of the disclosure. Accordingly, the disclosure is to be regarded as illustrative rather than restrictive.

The invention claimed is:

1. An endotracheal tube stabilizer comprising:
a stabilization bar; and
a tube cradle comprising:
a first component coupled to the stabilization bar, the first component comprising:
a concave portion;
a plurality of posts or a plurality of openings; and
a first tab and a second tab, the first and second tabs disposed on opposite sides of the concave portion;
a second component comprising:
a concave portion; and
the other of the plurality of posts or the plurality of openings, wherein each opening is configured to receive one of the posts when the first and second components are brought together, and wherein each of the posts is longer than a length of a corresponding opening that receives the post; and
an engagement element adapted to extend around the second component and selectively maintain the second component at a fixed location relative to the first component by engaging the first and second tabs to compress the endotracheal tube between the first and second components,
wherein the first and second components are adapted to translate toward one another in a direction generally normal to a length of the concave portions, wherein the concave portions of the first and second component together define an aperture adapted to receive an endotracheal tube, and wherein the aperture has a continuously arcuate surface around an entire perimeter of the aperture such that the aperture has 360 degrees of contact with the endotracheal tube along at least 90% of a length of the aperture.

2. The endotracheal tube stabilizer of claim 1, wherein the second component further comprising a guide portion including a pair of fingers canted towards one another to define an area through which the engagement element extends when engaged with the first and second tabs.

3. The endotracheal tube stabilizer of claim 2, wherein the stabilizer bar and the tube cradle are coated with an elastomeric coating.

4. The endotracheal tube stabilizer of claim 1, wherein the aperture has 360 degrees of contact with the endotracheal tube along at least 99% of the length of the aperture.

5. The endotracheal tube stabilizer of claim 1, wherein the first component is configured to be disconnected from the second component.

6. An endotracheal tube stabilizer comprising:
a stabilization bar; and
a tube cradle overmolded to the stabilization bar, the tube cradle comprising:
  a first component coupled to the stabilization bar, wherein the first component comprises:
    a concave portion;
    a plurality of posts or a plurality of recesses, wherein at least two of the plurality of posts or the plurality of recesses are disposed on a first side of the concave portion and at least one of the plurality of posts or the plurality of recesses is disposed on a second side of the concave portion, the second side opposite the first side;
    a first tab and a second tab, the first and second tabs disposed on opposite sides of the concave portion;
  a second component comprising:
    a concave portion;
    the other of the plurality of posts or the plurality of recesses, wherein the concave portions of the first and second components together define an aperture adapted to receive an endotracheal tube, and wherein the aperture is formed upon translating the first and second components toward one another in a direction generally normal to a length of the aperture with the plurality of posts and the plurality of recesses aligned with one another; and
    a guide portion disposed between two of the plurality of posts or two of the plurality of recesses, wherein the guide portion includes a pair of fingers canted towards one another to define a slot; and
  an engagement element adapted to extend around the second component to selectively maintain the second component at a fixed location relative to the first component by engaging the first and second tabs to compress the endotracheal tube between the first and second components, wherein the engagement element extends through the slot defined by the guide portion,
  wherein the aperture has a continuously arcuate surface around an entire perimeter of the aperture such that the aperture has 360 degrees of contact with the endotracheal tube along at least 90% of the length of the aperture.

7. The endotracheal tube stabilizer of claim 6, wherein the plurality of posts comprises:
at least one post extending from one of the first and second components on a first side of the aperture; and
at least one recess extending into the other of the first and second components on a second side of the aperture, the second side opposite the first side.

8. The endotracheal tube stabilizer of claim 7, wherein each of the plurality of posts has a length greater than a length of a corresponding recess.

9. The endotracheal tube stabilizer of claim 6, wherein the aperture defines an average diameter less than a diameter of the endotracheal tube.

10. The endotracheal tube stabilizer of claim 6, wherein the posts are disposed in the first component, and wherein the recesses are disposed in the second component.

11. The endotracheal tube stabilizer of claim 6, wherein the guide portion further comprises a second pair of fingers comprising fingers canted towards one another to form a slot, wherein the pair of fingers is disposed on a first side of the aperture, wherein the second pair of fingers is disposed on a second side of the aperture opposite the first side, and wherein the pair of fingers and the second pair of fingers are disposed directly across from one another with respect to the aperture.

12. The endotracheal tube stabilizer of claim 6, wherein the tube cradle is disposed at a central location along the stabilization bar.

13. The endotracheal tube stabilizer of claim 6, wherein the endotracheal tube stabilizer further comprises a plurality of cheek pads comprising a first cheek pad removably coupled at a first end of the stabilization bar and a second cheek pad removably coupled at a second end of the stabilization bar.

14. An endotracheal tube stabilizer comprising:
a stabilization bar extending between a first axial end and a second axial end;
a tube cradle comprising:
  a first component fixedly coupled to the stabilization bar, the first component comprising:
    a concave portion; and
    a plurality of posts or a plurality of openings, wherein the first component and the stabilization bar are coated with an elastomeric material; and
  a second component comprising:
    a concave portion;
    the other of the plurality of posts or the plurality of openings, wherein each opening is configured to receive one of the plurality of posts, wherein the posts extend entirely through the openings and are visible from an opposite side of the opening when the first and second components are coupled together; and
    a guide portion disposed between two of the plurality of openings, wherein the guide portion includes a pair of fingers canted towards one another to define a slot; and
  an engagement element that extends around the second component to selectively maintain the second component at a fixed location relative to the first component by engaging a first tab and a second tab to compress the endotracheal tube between the first and second components, wherein the engagement element extends through the slot defined by the guide portion; the first and second tabs disposed on opposite sides of the concave portion of the first component;
  wherein the concave portions together define an aperture adapted to receive an endotracheal tube, and wherein the aperture has a continuously arcuate surface around an entire perimeter of the aperture such that the aperture has 360 degrees of contact with the endotracheal tube along at least 90% of the length of the aperture; and
  a plurality of cheek pads comprising a first cheek pad removably coupled at the first end of the stabilization bar and a second cheek pad removably coupled at the second end of the stabilization bar.

15. The endotracheal tube stabilizer of claim 14, wherein each of the posts has a diameter that is less than 90% of a diameter of a corresponding one of the openings when the first and second components are coupled together.

16. The endotracheal tube stabilizer of claim 14, wherein the guide portion further comprises a second pair of fingers comprising fingers canted towards one another to form a slot, wherein the pair of fingers is disposed on a first side of the aperture, wherein the second pair of fingers is disposed on a second side of the aperture opposite the first side, and wherein the pair of fingers and the second pair of fingers are disposed directly across from one another with respect to the aperture.

17. The endotracheal tube stabilizer of claim 14, wherein the aperture is essentially free of planar surfaces.

18. The endotracheal tube stabilizer of claim 14, wherein the engagement element comprises a ring and wherein the ring is selectively engageable with the first and second tabs to secure the first and second components together.

19. The endotracheal tube stabilizer of claim 14, wherein the aperture is configured to prevent deformation of the endotracheal tube when the first and second components are translated toward one another.

\* \* \* \* \*